US008529471B2

(12) United States Patent
Holte (10) Patent No.: US 8,529,471 B2
(45) Date of Patent: Sep. 10, 2013

(54) METHOD AND SYSTEM FOR THE DETERMINATION OF RESIDUAL VOLUME IN PATIENTS HAVING AN ENTERAL FEEDING TUBE

(75) Inventor: Bo Holte, Charlottenlund (DK)

(73) Assignee: Holtech Medical, Charlottenlund (DK)

( * ) Notice: Subject to any disclaimer, the term of this patent is extended or adjusted under 35 U.S.C. 154(b) by 832 days.

(21) Appl. No.: 12/329,258

(22) Filed: Dec. 5, 2008

(65) Prior Publication Data

US 2010/0137746 A1 Jun. 3, 2010

Related U.S. Application Data (60) Provisional application No. 61/119,583, filed on Dec. 3, 2008.

(51) Int. Cl.
*A61B 5/00* (2006.01)
(52) U.S. Cl.
USPC .............. 600/584; 600/561; 604/28; 604/910
(58) Field of Classification Search
USPC ............. 600/561, 573, 581, 583, 301; 60/28, 60/910, 403; 604/28, 910, 403
See application file for complete search history.

(56) References Cited

U.S. PATENT DOCUMENTS

| | | | | |
|---|---|---|---|---|
| 2,230,218 A | * | 2/1941 | Asche | 604/43 |
| 4,403,992 A | * | 9/1983 | Bertellini et al. | 604/410 |
| 4,525,156 A | * | 6/1985 | Benusa et al. | 604/28 |
| 4,642,105 A | * | 2/1987 | Toter | 604/323 |
| 4,808,161 A | | 2/1989 | Kamen | |
| 5,433,216 A | * | 7/1995 | Sugrue et al. | 600/591 |
| 5,520,662 A | | 5/1996 | Moss | |
| 6,063,051 A | | 5/2000 | Stern | |
| 6,351,993 B1 | | 3/2002 | Schellenberg | |
| 6,447,472 B1 | | 9/2002 | Moss | |
| 6,482,170 B1 | * | 11/2002 | Andersen | 604/27 |
| 6,503,208 B1 | * | 1/2003 | Skovlund | 600/561 |
| 6,626,827 B1 | * | 9/2003 | Felix et al. | 600/156 |
| 6,659,974 B1 | | 12/2003 | Moss | |
| 6,949,092 B1 | | 9/2005 | Moss | |

(Continued)

FOREIGN PATENT DOCUMENTS

WO 2009/012441 A2 1/2009

OTHER PUBLICATIONS

PCT International Search Report and Written Opinion dated Jan. 13, 2011.

(Continued)

*Primary Examiner* — Sean Dougherty
*Assistant Examiner* — Michael C Stout
(74) *Attorney, Agent, or Firm* — Andrus, Sceales, Starke & Sawall, LLP (57) ABSTRACT

A method and system for determining the residual volume within a patient having a naso-enteral feeding tube. A collection container is coupled to the naso-enteral feeding tube and a physical force is applied to the collection container to prevent stomach fluid from flowing into the collection container. The physical force is removed from the collection container and the stomach fluid is allowed to flow into the collection container. The volume of fluid within the collection container is determined, which represents the gastric residual volume of the patient. At least a portion of the collected volume of stomach fluid is returned to the patient from the collection container.

9 Claims, 6 Drawing Sheets

(56) References Cited

U.S. PATENT DOCUMENTS

| | | | |
|---|---|---|---|
| 7,883,472 B2* | 2/2011 | Holte | 600/561 |
| 2004/0253179 A1* | 12/2004 | Chang | 424/9.1 |
| 2005/0171468 A1* | 8/2005 | Wood | 604/39 |
| 2006/0074335 A1* | 4/2006 | Ben-Oren et al. | 600/532 |
| 2007/0207554 A1 | 9/2007 | Lin et al. | |
| 2008/0103408 A1* | 5/2008 | Denton et al. | 600/549 |
| 2008/0219928 A1* | 9/2008 | Becker et al. | 424/9.1 |
| 2008/0281193 A1* | 11/2008 | Ben Oren et al. | 600/436 |
| 2010/0274225 A1* | 10/2010 | Nishtala | 604/514 |

OTHER PUBLICATIONS

Metheny et al., "How to Aspirate Fluid from Small-Bore Feeding Tubes", The American Journal of Nursing, vol. 93, No. 5, May 1993, pp. 86-88.

Metheny et al., "Gastric Residual Volume and Aspiration in Critically Ill Patients Receiving Gastric Feedings", American Journal of Critical Care, 16(6): 512-519, Nov. 1, 2008.

Pullen, "Measuring gastric residual volume", Nursing, 34(4): 18, Apr. 2004.

Davies et al., "Randomized comparison of nasojejunal and nasogastric feeding in critically ill patients", Crit Care Med 2002, vol. 30, No. 3, pp. 586-590.

Parrish et al., "Checking Gastric Residual Volumes: A Practice in Search of Science?", Nutrition Issues in Gastroenterology, Series #67, Oct. 2008.

"Bedside measurement of intra-abdominal pressure (IAP) via an indwelling naso-gastric tube: clinical validation of the technique", Collee et al., Intensive Care Medicine, 1993, pp. 478-480.

* cited by examiner

METHOD AND SYSTEM FOR THE DETERMINATION OF RESIDUAL VOLUME IN PATIENTS HAVING AN ENTERAL FEEDING TUBE

CROSS-REFERENCE TO RELATED APPLICATION

This application is based on and claims priority from U.S. Provisional Patent Application Ser. No. 61/119,583 filed on Dec. 3, 2008

FIELD OF THE INVENTION

The present disclosure generally relates to a method and apparatus for measuring residual volume in patients receiving enteral nutrition. More specifically, the present disclosure relates to a method and apparatus for measuring residual volume in which the residual volume is removed from the patient, evaluated, and returned to the patient or discarded, as deemed appropriate.

BACKGROUND OF THE INVENTION

Enteral nutrition is generally preferred over parenteral nutrition because of its lower cost, lower rate of complications, and effective preservation of gut structure and function. Many critically ill patients cannot tolerate naso-gastric tube feeding, developing manifestations of intolerance including nausea, vomiting, and abdominal distension and aspiration. Gastric residual volumes are widely used to evaluate feeding tolerance and gastric emptying. High gastric residual volumes raise concern about intolerance to gastric feeding and the potential risk for regurgitation and aspiration pneumonia. Furthermore, high gastric residual volumes may be one of the key contributing factors to intra-abdominal hypertension. Values of gastric residual volumes cited as being high in patients receiving naso-gastric feeding typically range from 75 to 500 ml.

Conventional use of gastric residual volume measurement obtained by aspiration via a syringe is a time consuming procedure. The size of standard syringes for this purpose is limited to 100 ml, which means that a residual volume of e.g. 300 ml will require three aspiration cycles. The aspirated volume must be stored temporarily in a container because a residual volume lower than a critical volume should be returned to the patient's stomach, using the syringe for the re-injection of the aspirated volume. If the total aspirated volume is higher than the critical volume, it will be discarded in its entity. The critical volume varies from hospital to hospital, but is typically 100-499 ml. The procedure of aspirating a patient's stomach will often be delayed because the naso-gastric tube may collapse in response to the negative pressure created when aspirating with the syringe.

SUMMARY OF THE INVENTION

The present disclosure relates to a method and system for determining the gastric residual volume of a patient. Specifically, the present disclosure relates to a system and method that determines the gastric residual volume of a patient by collecting stomach fluid from the patient in a collection container, measuring the volume of the collected fluid and returning the collected stomach fluid to the patient after the gastric residual volume has been measured.

In one embodiment of the present disclosure, a collection container is connected to a naso-gastric feeding tube already inserted into the patient through a collection conduit. The collection container is preferably a clear, flexible container that includes a series of volume markings, preferable on the exterior surface of the collection container. During normal feeding of the patient through the naso-gastric feeding tube, the collection container is elevated 50-100 cm above the mid-axillary line of the patient to prevent the flow of stomach fluid from the patient into the collection container.

When it is desired to determine the gastric residual volume of the patient, the collection container is lowered to a level below the mid-axillary line of the patient such that stomach fluid from within the patient's stomach flows (siphons) into the collection container. The volume of stomach fluid within the collection container can be determined by the volume markings on the exterior of the collection container. Excess fluid or air may be drained through a valve placed in the bottom of the collection container.

Once the gastric residual volume within the collection container is determined, the collection container is again elevated above the patient such that the contents of the collection container flows (siphons) back into the patient's stomach.

In one embodiment of the disclosure, the collection conduit extending between the naso-gastric feeding tube and the collection container is clear and includes a series of pressure markings, including a zero marking. In accordance with the method of the present disclosure, the collection container is elevated above the patient until the zero marking on the collection conduit is aligned with the mid-axillary line of the patient. When the zero marking is aligned with the mid-axillary line of the patient, a column of fluid, which may be feed solution or stomach fluid, is pushed into the collection conduit by the intra-gastric pressure (IGP) of the patient. The height of the column of fluid within the collection conduit is compared to the pressure markings on the collection conduit to determine the IGP of the patient.

In yet another alternate embodiment of the disclosure, a pressure transducer is placed in fluid communication with the collection conduit leading from the collection container to the naso-gastric feeding tube. A supply of flushing fluid flows at a low rate through the pressure transducer and into the collection conduit. The pressure transducer is operable to measure the pressure within the collection conduit, which in turn determines the IGP of the patient.

In another embodiment of the disclosure, the collection container is positioned within a pressure chamber. The height of the pressure chamber is fixed relative to the patient such that the collection container is generally aligned with the mid-axillary line of the patient. A supply of pressurized air enters into the pressure chamber to elevate the pressure of the collection container above the IGP of the patient. The elevated pressure on the collection container prevents the flow of stomach fluid into the collection container.

When it is desired to determine the gastric residual volume of the patient, the pressurized air within the pressure chamber is vented to atmosphere through a flow meter. As the pressurized air flows through the flow meter, a control unit monitors the amount of flow and the pressure within the pressure chamber to determine the gastric residual volume for the patient. Once the gastric residual volume has been determined, the control unit re-pressurizes the pressure chamber to return the volume of stomach fluid to the patient.

Various other features, objects and advantages of the disclosure will be made apparent from the following description taken together with the drawings.

BRIEF DESCRIPTION OF THE DRAWINGS

The drawings illustrate the best mode presently contemplated of carrying out the invention. In the drawings.

DETAILED DESCRIPTION OF THE INVENTION

Figure 1:
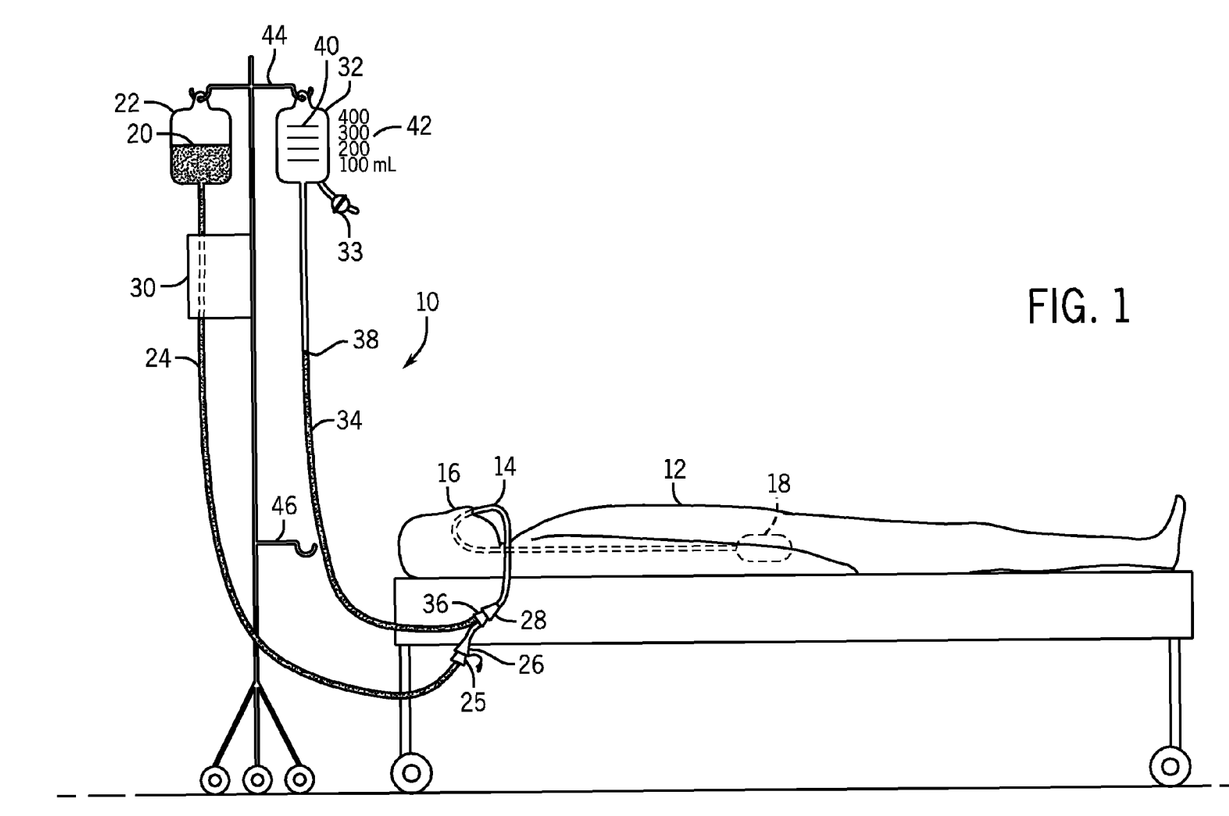
FIG. 1 is an illustration of a system to measure the gastric residual volume of a patient with a collection container in an elevated position.

FIG. 1 illustrates a system 10 to be used in measuring the gastric residual volume of a patient 12. As illustrated in FIG. 1, the patient 12 is in the supine position with a naso-gastric feeding tube 14 extending through the patient's nose 16 and being received within the stomach 18 or the jejunum. The naso-gastric feeding tube 14 allows a supply of liquid feed solution 20 to be fed into the patient's stomach 18 from a supply bag 22. The method and apparatus may be used for patients receiving enteral nutrition in the stomach, duodenum, or jejunum. The gastric route is most commonly used for enteral feeding and will be used in the present disclosure, to describe the invention.

In the embodiment shown in FIG. 1, the supply bag 22 is connected to a supply conduit 24 that includes a second end with a male connector 25 that is received by female connector 26. The female connector 26 is in fluid connection with male connector 36 that is received by a female connector 28 formed as part of the feeding tube 14.

In the embodiment illustrated, the supply of liquid feed solution from the supply bag 22 is pumped into the patient's stomach 18 by an enteral feeding pump 30, such as the Kangaroo Pump available from the Kendall Medical Company. The feeding pump 30 operates to push the liquid feed solution 20 through the supply conduit 24 and into the stomach 18 of the patient 12. Although a feeding pump is illustrated in the drawing figures, a gravity set placed well above the patient's mid-axillary line could also be used to supply the feed solution to the patient. In such an embodiment, a roller clamp and a drip counter chamber are used to supply the feed solution to the patient.

In addition to the supply of feed solution 20 and the supply bag 22, the naso-gastric feeding tube 14 is also coupled to a collection container 32 through a collection conduit 34. One end of the collection conduit 34 includes the female connector 26 and a male connector 36 that is received within the female connector 28 formed on the naso-gastric feeding tube 14.

When the patient 12 is receiving the supply of liquid feed solution 20 from the supply bag 22, the collection container 32 is elevated above the patient, as illustrated in FIG. 1. When the collection container 32 is elevated above the patient, the intra-gastric pressure (IGP) within the patient forces stomach fluid, which may be the feed solution, into the collection conduit 34 to a level 38 shown in FIG. 1. Since the collection container 32 is elevated well above the patient, the IGP of the patient is not sufficient to cause the stomach fluid from the patient 12 to flow against the force of gravity and into the open interior of the collection container 32.

In the embodiment shown in FIG. 1, the collection container 32 is a flexible, clear container that includes a series of volume markings 40 that can be labeled with volume indicators 42. The combination of the volume markings 40 and volume indicators 42 allows the volume of the collection container 32 to be determined without emptying the contents of the collection container 32.

As described previously, many critically ill patients cannot tolerate naso-gastric tube feeding. When monitoring these patients, gastric residual volumes are widely used to evaluate the feeding tolerance and gastric emptying. Specifically, when a patient is properly absorbing nutrients and feed solution, the feed solution is passed from the patient's stomach 18 into the intestinal tract. To conduct an evaluation of the gastric residual volumes, the volume of fluid within a patient's stomach 18 is determined and compared to the amount of feed solution directed to the patient through the supply conduit 24.

Figure 2:
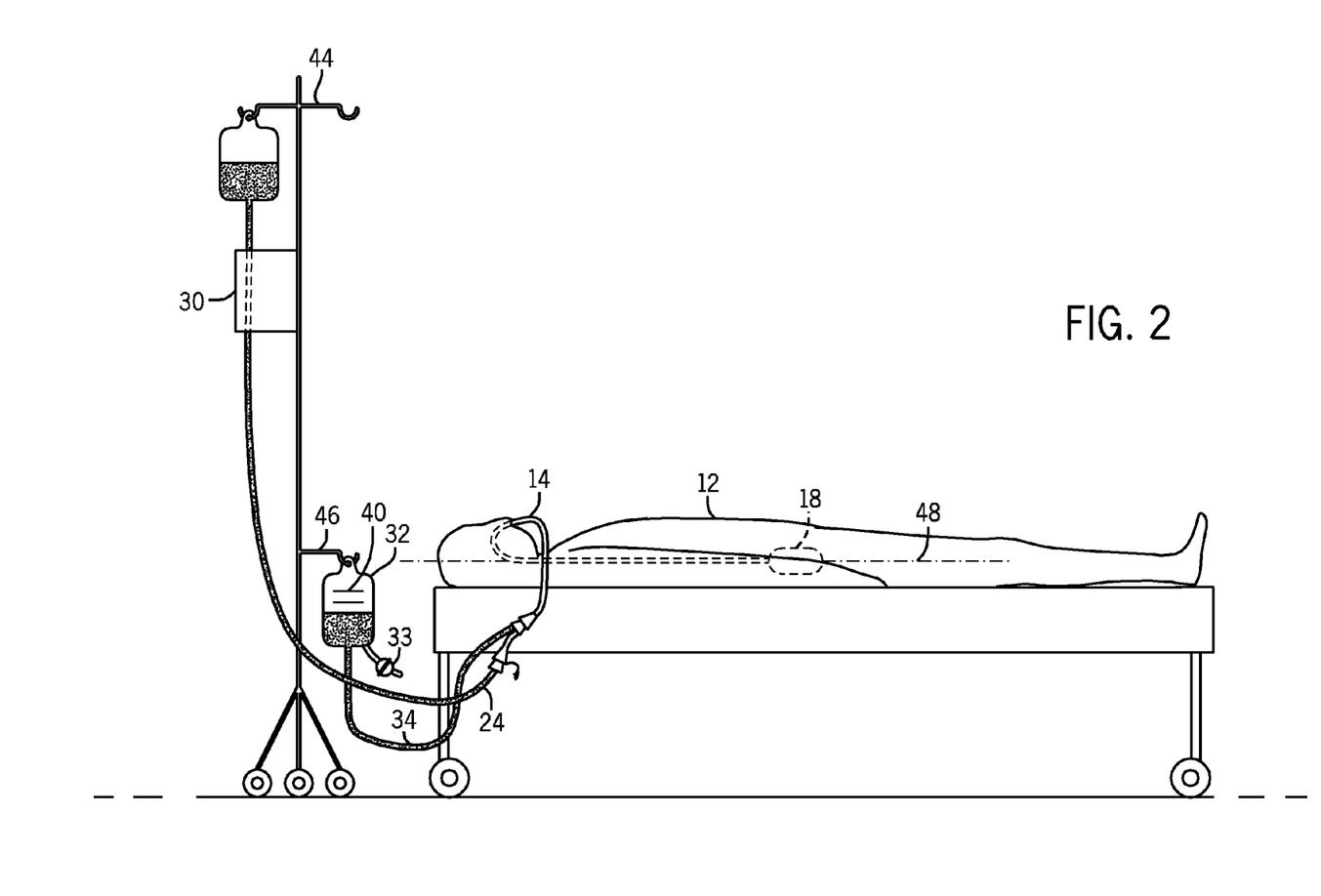
FIG. 2 is an illustration of the system of FIG. 1 with the collection container in the lowered, collection position.

Referring now to FIG. 2, when a gastric residual volume measurement is to be made, the collection container 32 is lowered from the elevated hanger 44 to a lower hanger 46 such that the collection container 32 is positioned below the mid-axillary line 48 of the patient.

When the collection container 32 is positioned below the mid-axillary line 48, the stomach fluid from within the patient's stomach 18 will flow (siphon) into the collection container 32 through the naso-gastric tube 14 and the collection conduit 34.

When the collection container 32 is positioned as shown in FIG. 2, the stomach fluid from the patient 12 begins to fill the open interior of the collection container 32. As the stomach fluid fills the collection container 32, the exterior markings 40 allow a user to determine the volume of fluid within the collection container 32. Preferably, the volume of the collection container 32 is selected to insure that the stomach fluid from the patient 12 will not overfill the collection container 32. In the case of overfilling, a drainage valve 33 may be activated and excess fluid or air may be drained from the collection container 32 into an external open container and subsequently discarded.

Once the stomach fluid from the patient 12 has been collected within the collection container 32, the gastric residual volume can be determined using the volume markings 40. If the gastric residual volume is below a critical volume, such as 400 ml, the stomach fluid can be returned to the patient. Stomach fluid is returned to the patient by once again elevating the collecting container 32 to the position shown in FIG. 1. In this position, the force of gravity causes the collected stomach fluid to flow (siphon) back into the patient's stomach through the collection conduit 34 and the naso-gastric tube 14.

If the gastric residual volume collected within the collection container 32 exceeds a critical volume, a portion of the stomach fluid can be withdrawn from the collection container through drainage valve 33 and discarded.

In the embodiment shown in FIGS. 1 and 2, the collection container can either be a soft-sided bag or a stiff-sided container that includes a vent to atmosphere. The venting to atmosphere allows the stiff-sided collection container to fill with the stomach fluid when the collection container is lowered to its collection position shown in FIG. 2.

Figure 3:
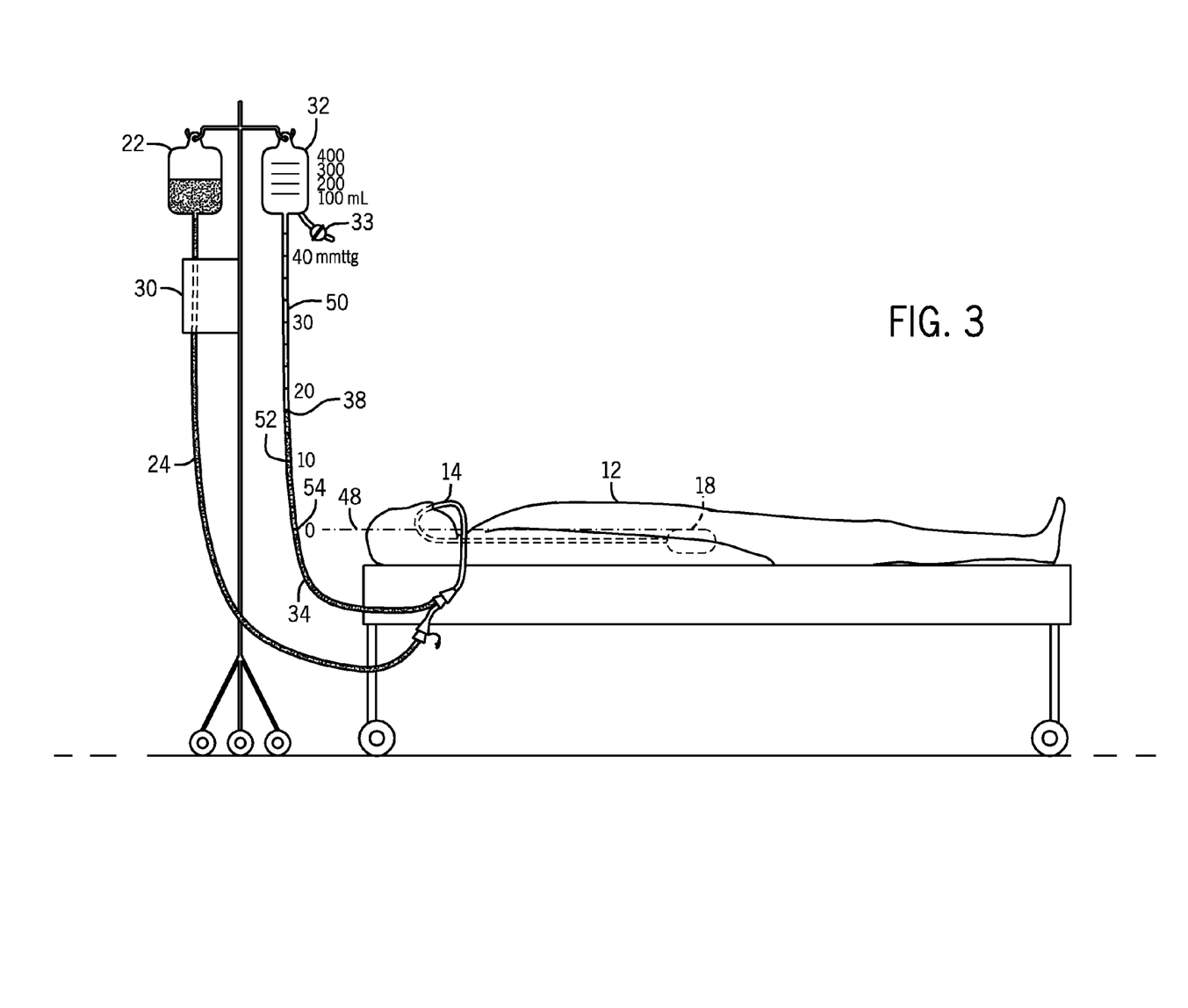
FIG. 3 is a first, alternate configuration of the system shown in FIG. 1 in which the collection tube includes markings to determine the intra-gastric pressure (IGP) of the patient.

Referring now to FIG. 3, thereshown is an alternate embodiment of the system for measuring the gastric residual volume of a patient. In the embodiment shown in FIG. 3, the collection conduit 34 is a transparent manometer tube that includes a series of pressure markings 50. Alternatively, a separate printed pressure scale (not shown) can be positioned adjacent to the collection conduit 34. Since the collection container 32 is either made form a flexible material or vented to atmosphere, the feeding solution and/or stomach fluid will enter the collection conduit 34 when the collection container 32 is elevated above the patient. The height of the fluid column in the collection conduit 34 reflects the intra-gastric pressure (IGP) of the patient 12.

When the user desires to make an IGP measurement for the patient, the collection container 32 is elevated above the patient until a zero marking 54 contained on the collection conduit 34 is aligned with the mid-axillary line 48 of the patient. Once the collection container is in this elevated position, the height of the fluid column 52 above the mid-axillary line 48 is indicative of the IGP.

In the embodiment shown in FIG. 3, the series of pressure markings 50 are used to determine the IGP. In the alternate embodiment employing the separate printed pressure scale, a zero marking on the printed pressure scale is aligned with the zero marking on the collection conduit 34. The level of fluid in the collection conduit is compared to the markings on the printed pressure scale to determine the IGP of the patient. The system shown in FIG. 3 can also be used as described in the discussion of FIGS. 1 and 2 to determine the gastric residual volume of the patient.

Figure 4:
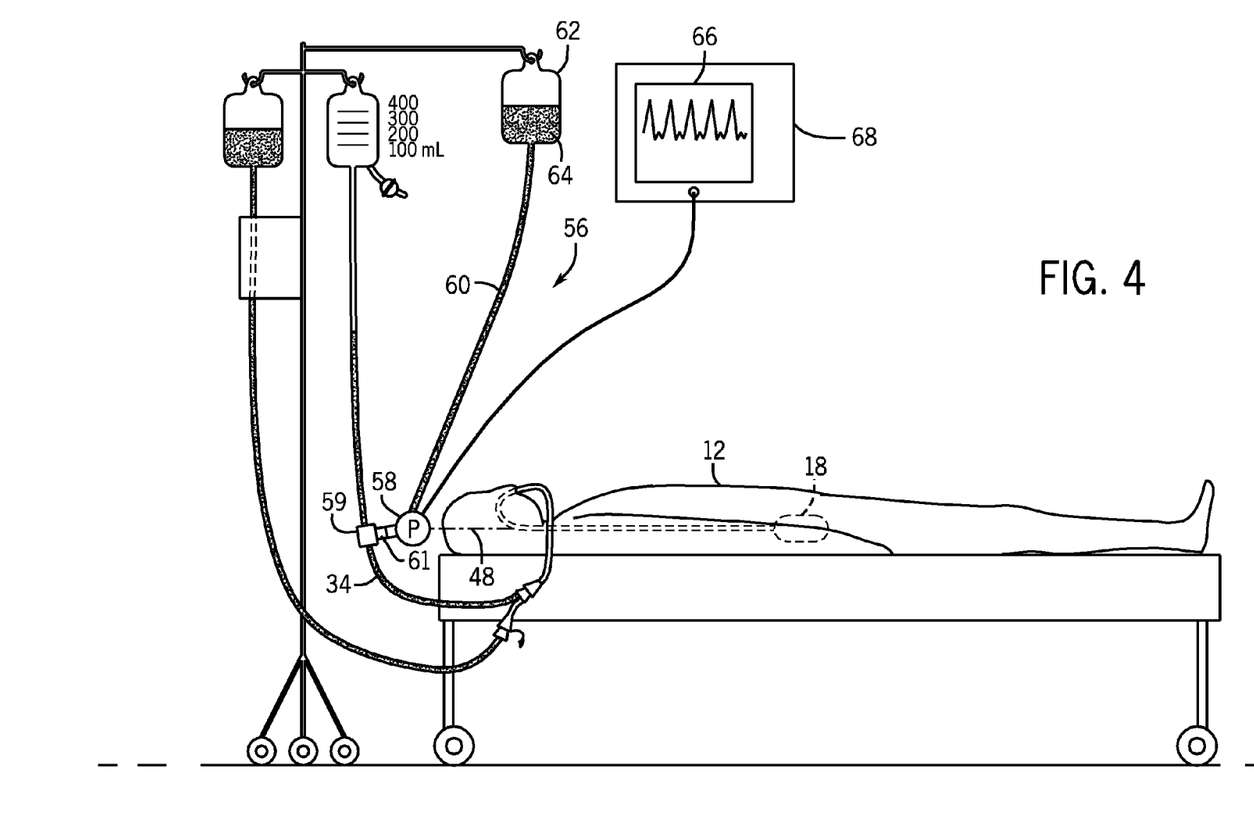
FIG. 4 is a second, alternate embodiment in which a supply of liquid is coupled to the collection conduit through a pressure sensor to determine the IGP of the patient.

In another embodiment shown in FIG. 4, the system includes an IGP sensing system 56. The IGP sensing system 56 includes a pressure transducer 58 generally aligned with the mid-axillary line 48 of the patient. The pressure transducer is of the type normally used for measurement of blood pressure, and includes a flow-resistance that limits the flow trough the transducer. The pressure transducer 58 is connected to a flushing conduit 60 extending between a supply 62 of a flushing fluid 64. Preferably, the flushing fluid 64 is sterile saline. The volume of the flushing fluid 64 flows through the pressure transducer 58 and into the collection conduit 34 through sensing conduit 61 and an inline connector 59. The flushing fluid flows through the collection conduit 34 and into the patient. Preferably, the flushing fluid 64 has a continuous flow rate of approximately 3 ml per hour or less to create continuous flushing of the pressure transducer 58.

As illustrated in FIG. 4, when the pressure transducer 58 is positioned aligned with the mid-axillary line 48 of the patient, the pressure of the fluid within the collection conduit 34 is directly related to the IGP of the patient. The pressure determined by the pressure transducer 58 can then be displayed on the display screen 66 of a patient monitor 68.

Figure 5:
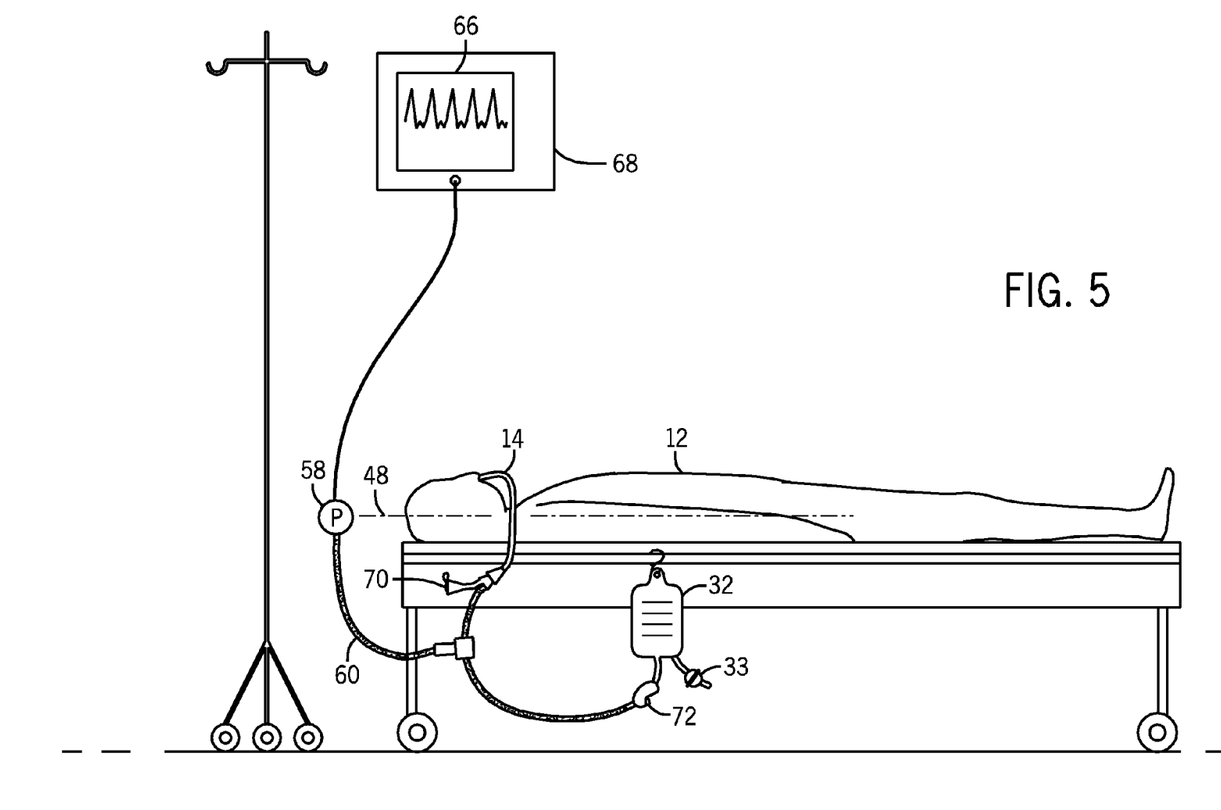
FIG. 5 is a third, alternate embodiment in which the naso-gastric feeding tube is not connected to a supply of feed solution.

In yet another embodiment shown in FIG. 5, the system of the present disclosure is shown being utilized with a patient 12 that is not yet receiving enteral feeding. In such an embodiment, the naso-gastric feeding tube includes a stopper 70 in a location where the supply conduit would typically be connected during enteral feeding. As shown, the collection container 32 is positioned below the patient with a clamp 72 preventing the flow of fluid into the collection container 32. In this embodiment, all of the conduits, including the naso-gastric tube 14 and the sensing conduit 60, are primed with sterile water or saline. When the pressure transducer 58 is positioned even with the mid-axillary line 48 of the patient, the pressure transducer can determine the IGP of the patient and relay this information to the display 66 of the patient monitor 68.

Figure 6:
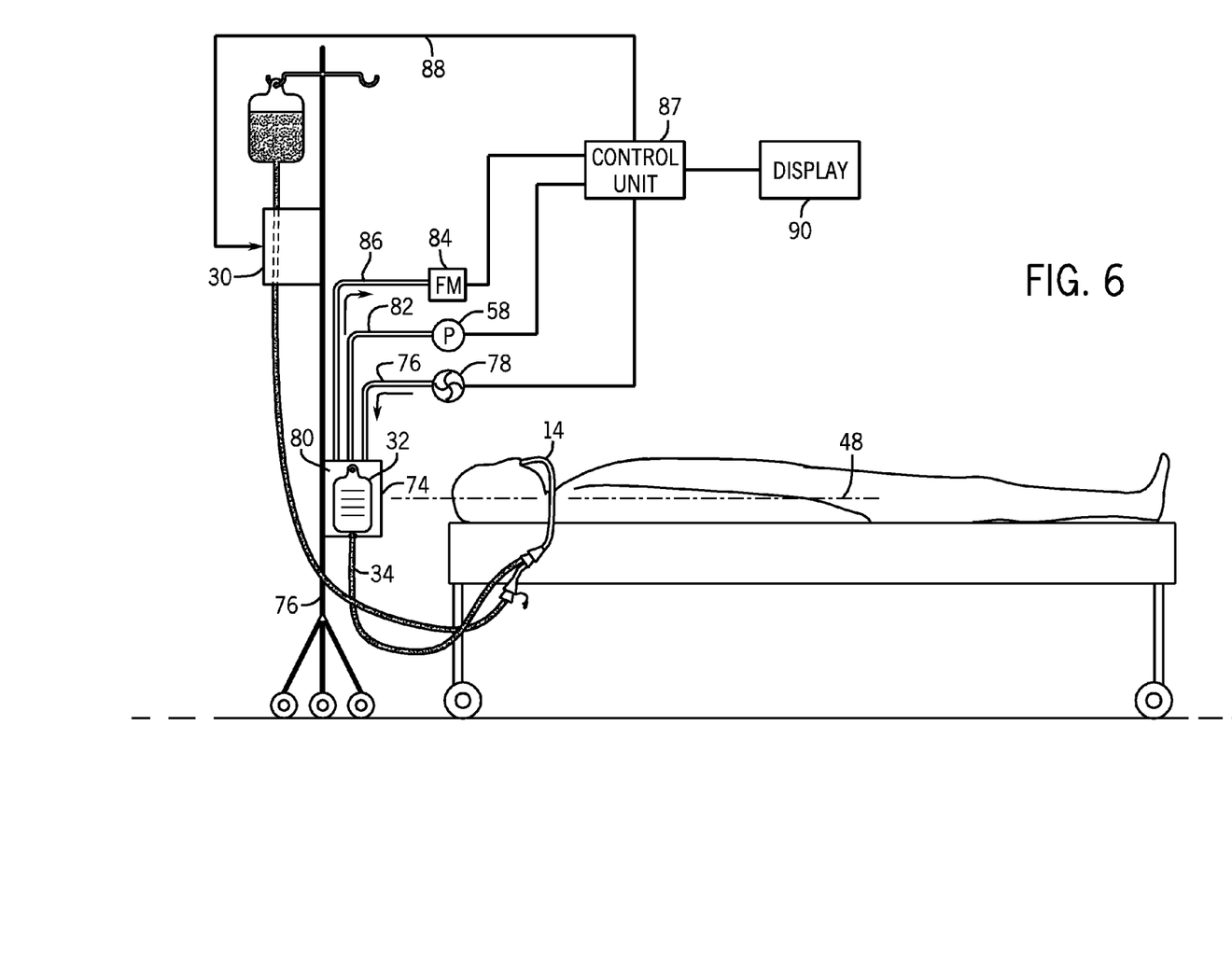
FIG. 6 is a fourth, alternate embodiment in which the collection container is pressurized using a supply of pressurized air.

FIG. 6 illustrates yet another embodiment of the system of the present disclosure. In the embodiment shown in FIG. 6, the collection container 32 is positioned within a pressurizing chamber 74. The collection container 32 is coupled to the naso-gastric feeding tube 14 through the collection conduit 34 as in the past embodiments. However, in the embodiment shown in FIG. 6, the collection container 32 is stationarily mounted to the stand 76 at a fixed location generally in line with the mid-axillary line 48. Although not illustrated in FIG. 6, the air-tight chamber 74 includes a door that can be opened to remove the collection container 32 as desired.

The air-tight chamber 74 is connected to an output 76 of an air pump 78 which is operable to pressurize the open interior 80 of the chamber 74. Pressure transducer 58 is also connected to the open interior 80 of the chamber 74 through a pressure conduit 82. Finally, an air flow meter 84 is connected to the open interior 80 through an air flow conduit 86. The control unit 87 is in communication with the feeding pump 30 through a communication cable 88.

During normal conditions, the air pressure within the open interior 80 of the chamber 74 is elevated above the IGP of the patient by operating the air pump 78. When the pressure within the open interior 80 is above the IGP for the patient, no fluid from the patient flows through the collection conduit 34 and into the empty collection container 32.

When it is desired to measure the gastric residual volume of the patient, a valve is opened in the air flow meter 84, thereby providing an air flow path to atmospheric pressure through the flow meter. The pressure transducer 58 measures the pressure drop within the open interior 80 and when the pressure within the open interior 80 has fallen to a steady value, which is equivalent to the patient's IGP, the air flow out of the pressure chamber 74 is calculated in the control unit 87 as the patient's stomach fluid fills the collection container 32. The air flow is calculated until the air flow drops to zero, indicating that the stomach is empty. At this time, the gastric residual volume has filled the flexible collection container 32 and the total air volume escaping the chamber 74 as the flexible collection container 32 fills with stomach fluid equals the gastric residual volume. The gastric residual volume may be calculated by associated electronic circuitry and software in control unit 87 by integrating the flow signal from the flow meter 84. Although not illustrated, the gastric residual volume and IGP can be displayed digitally on a patient monitor.

In addition to the display of the gastric residual volume, the gastric residual volume signal may be routed to the feeding pump 30 over the communication line 88 in order to adjust the rate of feeding. A high gastric residual volume may reduce the rate at which the feeding solution is supplied while a low gastric residual volume may justify an increase in the rate of feeding.

In addition to calculating the gastric residual volume, the system shown in FIG. 6 can also be used to determine the compliance of the stomach or the abdominal compartment. As discussed above, the pressure transducer 58 can determine the pressure within the open interior from when the collection container 32 begins to fill with the stomach fluid from the patient to a time when the collection container has filled with the entire contents of the patient's stomach. The pressure difference between the beginning and the end of the air flow out of the open interior 80 due to the filling of the collection container, together with the calculated gastric residual volume, can be used to calculate the compliance of the stomach or the abdominal compartment.

In accordance with the embodiment shown in FIG. 6, when the stomach contents have emptied completely into the collection container 32, the air pump 78 can be reactivated to pressurize the box and return the container's contents to the stomach of the patient. In one embodiment, it is contemplated that the gastric residual volume, IAP and compliance may be determined by the control unit 87 at regular intervals, such as once an hour, and displayed on a patient monitor or on a dedicated display module 90.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A method of measuring a gastric residual volume and an intra-gastric pressure (IGP) in a patient receiving a feeding solution through a naso-gastric feeding tube, the method comprising the steps of:
    positioning a collection container in fluid communication with the naso-gastric feeding tube, the collection container being sized to collect and measure a volume of stomach fluid from the patient anywhere within a critical range of at least 100 ml and up to 499 ml;
    elevating the collection container above the patient to prevent the flow of stomach fluid from the patient into the collection container;
    lowering the empty collection container below the patient such that the stomach fluid from within the patient's stomach flows into the collection container:
    measuring the volume of the stomach fluid in the collection container to determine the gastric residual volume of the patient;
    elevating the collection container including the collected stomach fluid above the patient to return the stomach fluid to the patient; and
    determining the intra-gastric pressure of the patient based upon the completed return of the stomach fluid to the patient.

2. The method of claim 1 wherein the collection container includes a series of volume markings to provide an indication of the volume of stomach fluid in the collection container.

3. The method of claim 1 wherein the collection container is coupled to the naso-gastric tube through a collection conduit, wherein the collection conduit includes a series of pressure markings.

4. The method of claim 3 wherein the series of pressure markings includes a zero marking, further comprising the steps of:
    elevating the collection container above the patient to return the stomach fluid to the patient, wherein the collection container is elevated such that the zero marking on the collection conduit is aligned with a mid-axillary line of the patient; and
    comparing the level of the fluid within the collection conduit to one of the series of pressure markings to determine the intra-gastric pressure of the patient.

5. The method of claim 1 wherein the collection container is coupled to the naso-gastric tube through a collection conduit, further comprising the steps of:
    elevating the collection container above the patient such that the stomach fluid returns to the patient and a zero marking is aligned with a mid-axillary line of the patient; and
    measuring the level of the fluid within the collection conduit using a printed scale having the zero marking and a series of pressure marking, wherein the printed scale is positioned adjacent to the collection conduit.

6. A method of measuring the gastric residual volume and intra-gastric pressure of a patient receiving a feeding solution through a naso-gastric feeding tube, the method comprising the steps of:
    connecting a collection container to the naso-gastric feeding tube through a collection conduit, wherein the collection conduit includes a series of pressure markings;
    elevating the collection container above the patient to prevent the flow of stomach fluid into the collection container during the flow of feeding solution to the patient;
    lowering the empty collection container below the patient following the supply of the feeding solution to the patient to allow stomach fluid to flow into the collection container;
    measuring the volume of stomach fluid in the collection container to determine the gastric. residual volume of the patient;
    elevating the collection container above the patient to return at least a portion of the collected stomach fluid to the patient;
    positioning the collection container above the patient such that a zero marking on the collection conduit is aligned with a mid-axillary line of the patient; and
    determining intra-gastric pressure of the patient based on the level of fluid within the collection conduit relative to at least one pressure marking.

7. The method of claim 6 wherein the collection container includes a series of volume markings to provide an indication of the volume of stomach fluid in the collection container, 8. A system for measuring the gastric residual volume and intra-gastric pressure of a patient receiving enteral feeding through a naso-gastric feeding tube, the system comprising:
    a transparent collection container in fluid communication with the naso-gastric feeding tube through a transparent collection conduit, wherein the collection container includes an open interior sized to collect and measure volumes of stomach fluid from the patient anywhere within a critical range of at least 100 ml and up to 499 ml to temporarily receive a gastric residual volume of stomach fluid from the patient;
    a series of volumetric markings included on the collection container to measure the collected gastric residual volume of stomach fluid from the patient;
    a drainage valve in fluid communication with the collection container, wherein the drainage valve is selectively opened to drain at least a portion of the stomach fluid from the open interior; and
    a series of pressure markings including a zero marking printed on the collection conduit, wherein the height of the stomach fluid in the collection conduit relative to the pressure marking indicates the intra-gastric pressure of the patient when the zero marking is aligned with a mid-axillary line of the patient.

9. The method of claim 1 wherein the step of determining the intra-gastric pressure includes utilizing a pressure sensor.

* * * * *